United States Patent [19]

Thomas

[11] Patent Number: 4,467,119
[45] Date of Patent: Aug. 21, 1984

[54] PHENOLIC ANTIOXIDANT

[75] Inventor: Royston Thomas, Middlesbrough, England

[73] Assignee: ICI Americas Inc., Wilmington, Del.

[21] Appl. No.: 491,359

[22] Filed: May 4, 1983

[51] Int. Cl.$^3$ .............................................. C07C 37/84
[52] U.S. Cl. ................................. 568/724; 568/720; 568/749
[58] Field of Search .................... 568/720, 724, 749

[56] References Cited

U.S. PATENT DOCUMENTS

| | | | |
|---|---|---|---|
| 3,196,185 | 7/1965 | Ranson | 568/720 |
| 3,205,189 | 9/1965 | Reed | 568/720 |
| 3,239,484 | 3/1966 | Stark | 568/720 |
| 4,242,527 | 12/1980 | Mark et al. | 568/724 |
| 4,319,051 | 3/1982 | Suenobu et al. | 568/720 |

FOREIGN PATENT DOCUMENTS

| | | | |
|---|---|---|---|
| 293612 | 4/1965 | Netherlands | 568/749 |
| 951939 | 3/1964 | United Kingdom | 568/724 |
| 1595309 | 8/1981 | United Kingdom | 568/724 |

*Primary Examiner*—Werren B. Lone
*Attorney, Agent, or Firm*—Louis F. Kreek, Jr.

[57] ABSTRACT

A process of purifying tris(1-hydroxy-3-methyl-6-tert. butyl phenyl) butane comprises crystallizing it from an aromatic hydrocarbon having 6 to 9 carbon atoms to produce a product containing said hydrocarbon and removing at least part of the hydrocarbon from the product by washing it with a liquid consisting essentially of at least one water miscible alcohol and water.

7 Claims, No Drawings

PHENOLIC ANTIOXIDANT

This invention relates to tris(1-hydroxy-3-methyl-6-tert. butyl phenyl) butane, a phenolic antioxidant. More particularly, it concerns a process for producing that compound in a purified form.

We first described a group of novel phenolic derivatives having important antioxidant properties, and a process for their preparation, in United Kingdom Pat. No. 951,935 and the corresponding U.S. Pat. No. 3,196,185. Among the compounds which we described was tris(1-hydroxy-3-methyl-6-tert. butyl phenyl) butane. It was produced by condensing crotonaldehyde with 3-methyl-6-tert. butyl phenol. The product has for many years been sold under the Trade Mark "Topanol" CA.

The product may be produced by carrying out the condensation in a solvent, for example methanol, and in the presence of a condensing agent, for example hydrochloric acid. The crude product may be isolated as a solid and may then be washed with water, whereafter it may be recrystallised from toluene, for example. (See for example, page 2 lines 55–64 of the above specification). In another embodiment, the product may be obtained by adding an entraining agent, preferably toluene, to the reaction mixture, distilling the mixture to remove water of condensation and finally recovering the product by crystallisation from the remaining entraining agent. (See page 2, lines 23–24 of the above specification).

When the production of tris(1-hydroxy-3-methyl-6-tert. butyl phenyl) butane includes a final recrystallisation from a $C_6$ to $C_9$ aromatic hydrocarbon for example toluene, the product may contain a quantity of the hydrocarbon in the catalyst. For many antioxidant uses the presence of the said hydrocarbon may be acceptable but in some uses it may be desired to use a product from which the hydrocarbon has been at least partly removed. One way of producing the product with a minimum aromatic hydrocarbon content is to subject the product to controlled heating, to remove some at least of the hydrocarbon present. Another way is to carry out a recrystallisation from another solvent. Yet another way is to omit the crystallisation from the aromatic hydrocarbon but this is a desirable feature of the well-established production method.

We have therefore devised an alternative process for producing tris(hydroxy-3-methyl-6-tert. butyl phenyl) butane of low aromatic hydrocarbon content, which represents a readily achieved modification of the well-proven existing process.

According to the present invention a process of purifying tris(1-hydroxy-3-methyl-6-tert. butyl phenyl) butane comprises crystallising it from an aromatic hydrocarbon having 6 to 9 carbon atoms to produce a product containing said hydrocarbon and removing at least part of the hydrocarbon from the product by washing it with a liquid consisting essentially of at least one water-miscible alcohol and water.

The tris(1-hydroxy-3-methyl-6-tert. butyl phenyl) butane may be made by condensing crotonaldehyde with 3-methyl-6-tert. butyl phenol as described in U.K. Pat. No. 951,935. Aldol may be used as an alternative to crotonaldehyde if desired. In forming the desired product three molecules of 3-methyl-6-tert. butyl phenol condense with each molecule of crotonaldehyde or aldol.

The alcohol (or alcohols if more than one is employed) may be a monohydric, dihydric or trihydric alcohol and may have a straight- or branched-chain or cycloaliphatic structure. Preferably it contains a maximum of six carbon atoms, and while ethylene glycol and glycerol are believed to be suitable alcohols in appropriate circumstances, it is preferred that the alcohol be a $C_1$ to $C_6$ straight- or branched-chain or cycloaliphatic monohydric alcohol. Preferred alcohols therefore include methanol, ethanol, n- and isopropanol, n-, sec. and tert. butanol, n-amyl alcohol and cyclohexanol. Among these, methanol, ethanol, isopropanol and tert. butanol are preferred and methanol is particularly preferred. If desired, mixtures of alcohols may be employed, for example in order to achieve a balance between the desirable relevant properties of the individual alcohols.

The water content of the liquid depends upon the alcohol or alcohols selected but normally (when miscibility permits) will lie in the range of 10 percent to 90 percent by weight. When using a $C_1$ to $C_6$ monohydric alcohol, the process may be operated to particular advantage by employing a mixture containing between 50 and 90 percent by weight of water. Furthermore, within this range, a good balance between product yield on the one hand and low aromatic hydrocarbon content of the product on the other, may be obtained by using an alcohol/water mixture containing between 65 and 85 percent by weight of water. Ideally, the liquid is so formulated as to maximise the hydrocarbon removal while minimising the solubility of the tris-phenolic compound in the liquid. The solubility of the compound in the alcohol itself increases, in the case of homologous monohydric alcohols, as the carbon number of the alcohol increases; however, the solubility of the compound in water is very low. Therefore, in order to limit the solubility of the compound in the washing liquid, the water content of the liquid should preferably be increased with increasing alcohol carbon number.

The washing of the crystals of tris(hydroxy-3-methyl-6-tert. butyl phenyl) butane may conveniently be carried out at ambient temperature. Since, however, the solubility of the phenolic compound in the alcohol and in water varies with temperature, it is possible to carry out the washing at an elevated temperature, say 60° C., to enable the use of a different alcohol or a different water content, from that which is appropriate at ambient temperature—for example to make possible the use of less alcohol in the aqueous alcohol wash mixture.

The quantity of aqueous alcohol employed conveniently is such that its weight is 1 to 5 times the weight of the phenolic compound. The optimum quantity may be determined by experiment and depends upon such factors as the composition of the aqueous alcohol, the desired purity of the washed product and the wash procedure selected. Often the optimum quantity will be 2 to 3 times the weight of the phenolic compound.

After the washing, the wet crystals may be subjected to drying, for example at an elevated temperature of 60° C. to 80° C., to remove residual wash liquor.

The invention is illustrated by the following Examples, in which percentages are by weight.

EXAMPLES 1 TO 3

246 g of 3-methyl-6-tert. butyl phenol (1.5 moles), 175 g of methanol and 87.5 g of concentrated hydrochloric acid were heated together, with stirring, until the methanol refluxed gently and then 35 g of crotonaldehyde (0.5 mole) was added slowly while the mixture was stirred. The resulting mixture was then held under reflux for a further one hour. A solution of anhydrous sodium carbonate (13 g in 150 ml water) was then added to neutralise the catalyst acid.

Methanol was distilled from the stirred reaction mixture until the temperature reached 98° C. and then 750 g of toluene was slowly added to dissolve the crude tris(hydroxy-3-methyl-6-tert. butyl phenyl)butane. The mixture separated into two layers and the lower (aqueous) layer containing dissolved neutralisation products was drained off, the upper (organic) layer being maintained at about 85° C.

The organic layer was now washed twice with 250 ml of water and finally the organic layer was allowed to cool to room temperature with stirring. The tris-phenolic product which crystallised out was filtered off and allowed to dry. The product was analysed and found to contain 1.2 percent of water, 2.6 percent of methanol and 11.1 percent of toluene.

A 50-gm portion of this primary product was subjected to washing with 200 ml of a methanol/water mixture, the phenolic compound and the mixture being mixed together over a period of 30 minutes before removal of the washed product by filtration. The product was now dried in a fan-assisted oven for 4 hours at a temperature of 69° C. Finally, the dried product was weighed and analysed for water, methanol and toluene, with the following results:

| Example No. | Water in Wash Liquid (% wt) | Product Weight (gm.) | Product Analysis (% wt) | | |
|---|---|---|---|---|---|
| | | | Water | Methanol | Toluene |
| 1 | 24 | 42.9 | 1.0 | 3.7 | 0.3 |
| 2 | 56 | 44.0 | 0.38 | 0.5 | 2.7 |
| 3 | 75 | 43.7 | 0.24 | 0.6 | 2.0 |

EXAMPLE 4

A 50-gm portion of tris(hydroxy-3-methyl-6-tert. butyl phenyl) butane, prepared as described in the above Examples (the "primary product" following crystallisation from the organic layer), was washed for half-an-hour with 200 ml of aqueous isopropanol containing 75 percent of water and then separated by filtration. Drying the solid for four hours at 70° C. yielded 47.4 gm of product which on analysis was found to contain 0.27 percent of water, 9.3 percent of isopropanol and only 0.4 percent of toluene.

EXAMPLE 5

The preceding Example was repeated using 50 gm of phenolic compound and 200 ml of aqueous tert. butanol containing 75 percent of water. 50.0 gm of product was obtained, containing 0.23 percent of water, 14.6 percent of tert. butanol and only 0.7 percent of toluene.

EXAMPLE 6

246 g of 3-methyl-6-tert. butyl phenol (1.5 moles), 175 g of methanol and 87.5 g of concentrated hydrochloric acid were heated together, with stirring, until the methanol refluxed gently and then 35 g of crotonaldehyde (0.5 mole) was added slowly while the mixture was stirred. The resulting mixture was then held under reflux for a further one hour. A solution of anhydrous sodium carbonate (13 g in 150 ml water) was then added to neutralise the catalyst acid.

Methanol was distilled from the stirred reaction mixture until the temperature reached 98° C. and then 750 g of toluene was slowly added to dissolve the crude tris(hydroxy-3-methyl-6-tert. butyl phenyl) butane. The mixture separated into two layers and the lower (aqueous) layer containing dissolved neutralisation products was drained off, the upper (organic) layer being maintained at about 85° C.

The organic layer was now washed twice with 250 ml of water and finally the organic layer was allowed to cool to room temperature with stirring. The tris-phenolic product which crystallized out was removed. The product at this stage was found to contain 10.8 percent of toluene and 1.5 percent of water.

The crystals were now washed with 450 ml of aqueous methanol, containing 25 percent by weight of water. After this wash treatment and subsequent drying for 4 hours in a fan-assisted oven at 68° C., the crystals were now found to contain 2.5 percent of water, 3.4 percent of methanol and only 0.8 percent of toluene.

I claim:

1. A process for purifying tris(1-hydroxy-3-methyl-6-tert. butyl phenyl) butane which comprises:
    (a) adding an aromatic hydrocarbon having from 6 to 9 carbon atoms to impure product tris(1-hydroxy-3-methyl-6-tert. butyl phenyl) butane and recrystallizing said product from said aromatic hydrocarbon, thereby producing a recrystallized product containing said hydrocarbon;
    (b) washing said recrystallized product with a liquid consisting essentially of at least one water-miscible $C_1$ to $C_6$ straight or branched chain or cycloaliphatic monohydric alcohol and water, thereby removing at least part of said hydrocarbon; and
    (c) recovering purified product tris(1-hydroxy-3-methyl-6-tert. butyl phenyl) butane.

2. A process according to claim 1 in which the tris(1-hydroxy-3-methyl-6-tert. butyl phenyl) butane is produced by condensing 3 molecules of 3-methyl-6-tert. butyl phenol with crotonaldehyde or aldol.

3. A process as claimed in claim 1 in which the alcohol is a $C_1$ to $C_6$ straight or branched chain or cycloaliphatic monohydric alcohol.

4. A process as claimed in claim 3 in which the alcohol is methanol, ethanol, isopropanol or tertiary butanol.

5. A process as claimed in claim 1 in which the water content of the wash liquid is in the range 10% to 90% by weight.

6. A process as claimed in claim 1 in which the tris(1-hydroxy-3-methyl-6-tert. butyl phenyl) butane is prepared by condensing crotonaldehyde with 3-methyl-6-tert. butyl phenol in a 1:3 molar ratio.

7. A process as claimed in claim 1 including the further step of drying the washed product of step (b) at a temperature of 60° C. to 80° C. to remove residual wash liquid.

* * * * *

UNITED STATES PATENT AND TRADEMARK OFFICE
CERTIFICATE OF CORRECTION

PATENT NO. : 4,467,119
DATED : August 21, 1984
INVENTOR(S) : Royston Thomas

It is certified that error appears in the above-identified patent and that said Letters Patent are hereby corrected as shown below:

Assignee: reads "ICI Americas Inc., Wilmington, Del."

should read --Imperial Chemical Industries PLC
Millbank, London, England--

Signed and Sealed this

Fifteenth Day of January 1985

[SEAL]

Attest:

GERALD J. MOSSINGHOFF

Attesting Officer

Commissioner of Patents and Trademarks